United States Patent
Quistorff et al.

(10) Patent No.: US 6,701,171 B2
(45) Date of Patent: Mar. 2, 2004

(54) METHOD AND APPARATUS FOR NON-INVASIVE DETECTION OF ANGIOGENIC AND ANTI-ANGIOGENIC ACTIVITY IN LIVING TISSUE

(75) Inventors: Bjørn Quistorff, Charlottenlund (DK); Paul E. G. Kristjansen, Hørsholm (DK); Michael Kragh, Copenhagen (DK)

(73) Assignee: Københavns Universitet, Copenhagen K (DK)

( * ) Notice: Subject to any disclaimer, the term of this patent is extended or adjusted under 35 U.S.C. 154(b) by 224 days.

(21) Appl. No.: 09/778,923

(22) Filed: Feb. 8, 2001

(65) Prior Publication Data

US 2001/0035503 A1 Nov. 1, 2001

(30) Foreign Application Priority Data

Mar. 31, 2000 (DK) .......................... 2000 00546

(51) Int. Cl.[7] .............................. A61B 5/00; A61B 5/02
(52) U.S. Cl. ...................................... 600/328; 600/504
(58) Field of Search ................................ 600/310, 322, 600/323, 326, 328, 481, 483, 500, 504

(56) References Cited

U.S. PATENT DOCUMENTS

| | | | |
|---|---|---|---|
| 4,213,462 A | * | 7/1980 | Sato .......................... 600/477 |
| 5,233,994 A | | 8/1993 | Shmulewitz |
| 5,253,646 A | | 10/1993 | Delpy et al. |
| 5,291,885 A | | 3/1994 | Taniji et al. |
| 5,293,873 A | | 3/1994 | Fang |
| 5,810,010 A | | 9/1998 | Anbar |
| 5,853,370 A | | 12/1998 | Chance et al. |
| 6,064,898 A | | 5/2000 | Aldrich |
| 6,381,018 B1 | * | 4/2002 | Bigio et al. .................. 600/476 |
| 6,405,070 B1 | * | 6/2002 | Banerjee ..................... 600/477 |

OTHER PUBLICATIONS

Okunieff et al., "Radiation–Induced Changes In Bone . . . ", Int. J. Radiation Oncology Biol. Phys., vol. 42, No. 4, 1998, pp. 885–889.

Smielewski et al., "Clinical Evaluation of Near–Infrared Spectroscopy . . . ", Stroke, vol. 28, No. 2, Feb. 1997, pp. 331–338.

Rendell et al., "Determination of blood flow in the finger . . . ", Clinical Physiology, 18, 5, pp. 426–434, 1998, Blackwell Science Ltd.

Jain et al., "Quantitative angiogenesis assays . . . ", Nature Medicine, vol. 3, No. 11, Nov. 1997, pp. 1203–1208.

Brazy et al., "Noninvasive Monitoring of Cerebral . . . ", Pediatrics, vol. 75, No. 2, Feb. 1985, pp. 217–225.

Chance et al., "Time–Resolved Spectroscopy of Hemoglobin . . . ", Analytical Biochemistry, 174, pp. 698–707, 1988.

Kirkpatrick et al., "Resolving extra– and interacranial signal . . . ", Neurological Research, vol. 20, 1998, Supp. 1 (pp. S19–S22), Forefront Publishing Group.

(List continued on next page.)

Primary Examiner—Eric F. Winakur
(74) Attorney, Agent, or Firm—Birch, Stewart, Kolasch & Birch, LLP

(57) ABSTRACT

The present invention relates to a method for non-invasive local quantification of angiogenesis or destruction of existing blood vessels in living tissue, the use of the said method for local measurements of hemoglobin concentration and blood perfusion at the same location on the subject and an apparatus for carrying out the method according to the invention. The apparatus comprises a xenon flash unit, an optical filter and a Y-shaped optical fiber-bundle, one branch of the fiber-bundle being coupled to the flash unit and the other branch of the fiber-bundle being coupled to a detection unit and the merged part of the fiber-bundle being adapted to couple the apparatus to the tissue to be tested.

9 Claims, 10 Drawing Sheets

OTHER PUBLICATIONS

Lam et al., "Internal and External Carotid Contributions . . . ", *Stroke*, vol. 28, No. 5, May 1997, pp. 906–910.

Kirkpatrick et al., "Near–infrared spectroscopy use . . . ", *J. Neurosurg.*, vol. 83, Dec. 1995, pp. 963–970.

Abbott et al., "Laser Doppler Perfusion Imaging . . . ", *Journal of Investigative Dermatology*, vol. 107, No. 6, Dec. 1996, pp. 882–886.

Padubidri et al., "Effect of Vascular Endothelial Growth Factor . . . ", *Annals of Plastic Surgery*, vol. 37, No. 6, Dec. 1996, pp. 604–611.

* cited by examiner

METHOD AND APPARATUS FOR NON-INVASIVE DETECTION OF ANGIOGENIC AND ANTI-ANGIOGENIC ACTIVITY IN LIVING TISSUE

BACKGROUND FOR THE INVENTION

1. Field of the Invention

The present invention relates to a method for non-invasive local quantification of angio-genesis or elimination of existing blood vessels in living tissue, to the use of near infrared spectroscopy and/or laser doppler flowmetry for local measurements of hemoglobin concentration and blood perfusion at the same location on the subject, and to an apparatus for non-invasive quantification of angiogenesis or elimination of blood vessels in living tissue.

2. Background Art

In normal tissue many important processes such as wound healing, tissue growth and the development of the fetus during pregnancy involves the formation of new blood vessels (capillaries). This process of vascularisation also known as angiogenesis is of paramount importance since supply of nutrients including oxygen as well as removal of waste products constitute an absolute prerequisite for survival and growth.

In cancerous tissue, tumors cannot grow or spread (metastasize) without the development of new blood vessels. Solid tumors cannot grow beyond the size of a pin-head (1 to 2 cubic millimeters) without inducing the formation of new blood vessels to supply the nutritional needs of the tumor.

Endothelial cells, that form the walls of blood vessels, are the source of new blood vessels. The creation of new blood vessels occurs by a series of sequential steps whereby the endothelial cells forming the wall of an existing small blood vessel (capillary) become activated and start to invade the matrix creating new networks of blood vessels which makes tissue growth possible. New capillary growth is tightly controlled by a finely tuned balance between factors that activate endothelial cell growth and those that inhibit it.

In recent years the process of angiogenesis has been realized as a potential target for anti-tumor growth since any therapy which will prevent the angiogenesis will inherently restrict tumor growth.

Since hemoglobin is a strong absorber of light, it has been known for a long time that hemoglobin concentration can be quantified by spectroscopic techniques. Also since the absorption of hemoglobin changes during oxygenation/deoxygenation it is well known that the oxygenation state of hemoglobin in tissue may be quantified. The absorption spectrum of hemoglobin and deoxyhemoglobin is characteristically different also in the near infrared region of the spectrum (700–1100 nm), where the absorption in water (and hence in tissue) is relatively small. This has led to the development of NIRS (near infrared spectroscopy) of tissues, with instrumentation by which it is possible to evaluate the oxygenation of a given tissue region (e.g. Brazy et al. 1985, Pediatrics 75:217–225; Chance et al. 1988, Anal. Biochem. 174:698–707).

As concluded in a review by R. K. Jain et al (Nature Medicine, 1997,3: 1203–1208), a prerequisite to answering important questions about the biology of angiogenesis and to effectively seek out new therapeutic agents, with beneficial effects on angiogenesis, is the availability of a quantitative, rapid and routine angiogenesis assay. Furthermore the authors have stated, that such an assay has not been currently available.

Existing in vivo assays can be divided into three categories: Exteriorized tissue preparations, chronic transparent chambers and other in situ preparations including artificial matrix implants, and excised tissues. Overall the assays were only quantitative at the expense of the tissue integrity, and thus forfeiting the potential for repeated measurements (monitoring). Existing assays, on the other hand, are either not quantitative or they are based on quite complicated micro surgical procedures, which are prohibitively expensive and too time-consuming for screening purposes.

Selective blocking of each of the six principal steps in the angiogenic cascade can lead to inhibition or halting of tumor growth. Since the mid-1990ties many pharmaceutical companies involved in cancer therapeutics have focused intensely on the development of anti-angiogenic compounds, and approximately 30 compounds have already been through various phases of clinical testing. In parallel, a series of related compounds, which by different mechanisms destroy existing blood vessels in tumors are under development. This category of experimental cancer drugs is called vascular targeted agents. They destroy existing vasculature and make tumors shrink, whereas anti-angiogenic agents obstruct further growth and spread of small tumors by preventing the formation of essential new vascular networks.

In order to develop and test new cancer therapeutic agents it is desirable to provide a fast, reproducible method which makes it possible to monitor changes in angiogenesis or destruction of blood vessels versus time in response to application or administration of anti-angiogenic therapeutic agents or vascular targeting agents to a subject. This requires a non-invasive method which will not affect the viability of the localized tissue cells. Since angiogenesis involves the formation of new capillaries, measurement of changes versus time of total hemoglobin in a specific location will also provide a quantitative or at least semi-quantitative measure of local angiogenesis. Likewise, the formation of new blood vessels will result in a local increase in blood perfusion versus time.

SUMMARY OF THE INVENTION

Accordingly it is an object of the present invention to provide a simple method for measuring the relative local changes in hemoglobin concentration and/or blood perfusion. The method shall be non-invasive and non-harmful to the tissue and the subject. In this way measurements can be performed on the same subject repeatedly and for long periods of time. In order to save time consuming measurements involving separate measurements for each parameter and at the same time ensure that both parameters to be measured are done so at the exact same location on the tissue of the subject it is also an object of the invention to provide an apparatus facilitating simultaneous measurement of NIRS (near infrared spectroscopy) and LDF (laser doppler flowmetry) at the same location. According to a first aspect of the invention, these and other objects are accomplished by providing a method for non-invasive local quantification of angiogenesis or quantification of elimination of existing blood vessels in living tissue comprising near infrared spectroscopy (NRS) for measuring total hemoglobin concentration and/or Laser Doppler Flowmetry (LDF) for measuring the average blood perfusion of the same location.

The invention also provides a method for local non-invasive measurement of hemoglobin concentration and blood perfusion at the same location on the subject after application or administration of a substance chosen from the group comprising anti-angiogenic agents, vascular targeting agents, anti-inflammatory agents, skin transplants, or any agent that will affect blood circulation. The method consists of a near infrared spectroscopy (NIRS) measurement, and a laser doppler flowmetry (LDF) measurement performed at the same location and substantially at the same time. The performed measurements of NIRS and LDF can be continuously repeated in order to monitor the time dependent response after application or administration of the above agents.

According to a second aspect the invention also relates to an apparatus for non invasive quantification of angiogenesis or quantification of destruction of existing blood vessels in living tissue comprising a xenon flash unit, an optical filter, and a Y-shaped optical fiber bundle, one branch of the fibre bundle being coupled to the flash unit and the other branch of the fiber bundle being coupled to the detection unit, while the merged part of the fibre bundle may be coupled to the probe of the LDF equipment in such a way that the NIRS and the LDF measurements originate from nearly the same tissue location when the merged NIRS/LDF probe is placed on the tissue surface.

According to a third aspect of the invention there is also provided a use of near infrared spectroscopy and laser doppler flowmetry for local measurements of hemoglobin concentration and blood perfusion at the same location on the subject after application or administration of a substance chosen from the group comprising, anti-angiogenic agents, vascular targeted agents, skin agents, skin transplants, or any agent that will affect blood circulation.

BRIEF DESCRIPTION OF THE DRAWING

The invention is explained in detail below with reference to the drawing, in which.

DETAILED DESCRIPTION OF PREFERRED EMBODIMENTS

Figure 1A:
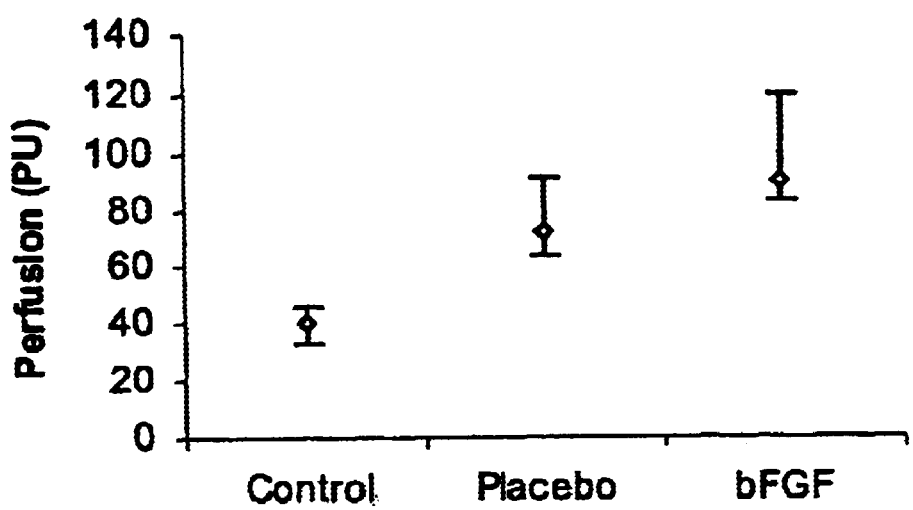
FIG. 1A shows the induced angiogenic response in a mouse model after application of fibroblast growth factor (bFGF) measured by LDF.

A method for non-invasive local quantification of angiogenesis or quantification of elimination of existing blood vessels in living tissue comprises the steps of (i) performing a near infrared spectroscopy (NIRS) measurement of total haemoglobin concentration and (ii) performing a Laser Doppler Flowmetry (LDF) measurement of the average blood perfusion.

The method applies a novel flash-based near infrared spectrometer (NIRS) and a commercially available Laser-doppler-flow instrument. The NIRS instrument permits a non invasive estimation of the total hemoglobin content of a given tissue volume, while the LDF instrument provides a measure of the average speed of movement of the red blood cells (RBC's) in the tissue volume. The hemoglobin determination will provide a measure of the capillary volume and the LDF of the flow. As a result, the product of the two measurements will give an estimation of the bulk flow of the tissue volume under observation. By combining NIRS and LDF the significant fraction of still unfused vascular branches (cul-de-sacs), loaded with red blood cells, but with no movement whatsoever, are accounted for, which they could not have been with LDF alone. Correspondingly, the balance between the dynamic measurements of the LDF and the more static parameter obtained by NIRS, will contain important information of the degree of extravascular blood pools (hematoma), which e.g. in the matrix implant models, represents sources of severe bias in the determination of vascular volumes.

The method according to the invention makes it possible to correct for the above mentioned bias. The present invention provides a method for non-invasive local quantification of angiogenesis or quantification of elimination of existing blood vessels in living tissue wherein NIRS and LDF are combined and result in a quantitative local measure of angiogenic activity or a local measure of the elimination of existing blood vessels, said quantification being obtained by means of a novel flash-based near infrared spectrometer and a laser doppler flow instrument.

The method according to the invention may be used in the study of a group of compounds called angiogenesis inhibitors. These are drugs that block angiogenesis thereby preventing the tumor from growing and hence its continued spread to other parts of the body. In the study and development of such drugs or therapeutic agents a method allowing a direct measurement of angiogenesis on the subject will be very useful.

Another type of related cancer therapy agents which by different mechanisms eliminate existing blood vessels in tumors are under test and development. This category of experimental cancer drugs is called vascular targeted agents and by eliminating existing blood vessels they make tumors shrink. The method according to the invention may also be used in the study of this group of agents.

According to the method of the present invention the continuous quantification of changes in the composition and function of the blood capillaries in living tissue makes it possible to use said method for testing skin agents, anti-inflammatory agents, or any therapeutic agent or treatment which will affect the blood circulation. Also the quality and state of skin transplants can be tested by means of the method according to the invention.

The method according to the invention further allows the repeated measurement on the same subject for long periods of time, which will result in the use of less subjects/animals and a more differentiated information since the progress in the angiogenic or anti-angiogenic development can be monitored in the individual subject.

A further aspect of the present invention therefore relates to a method for local non-invasive measurement of hemoglobin concentration and blood perfusion at the same spot on the subject after application or administration of a substance chosen from the group comprising anti-angiogenic agents, vascular targeting agents, anti-inflammatory agents, skin transplants, or any agent that will affect blood circulation, by performing a near infrared spectroscopy measurement, and performing a laser doppler flowmetry measurement. The performed measurements of NIRS and LDF can be continuously repeated in order to monitor the time dependent response after application or administration of the above agents.

It is also an aspect of the invention to use near infrared spectroscopy and laser doppler flowmetry for local measurements of hemoglobin concentration and blood perfusion at the same location on the subject after application or administration of a substance chosen from the group comprising anti-angiogenic agents, vascular targeting agents, anti-inflammatory agents, skin transplants, or any other agents that will affect the blood circulation of the subject.

The apparatus for non-invasive local quantification of angiogenesis or quantification of elimination of existing blood vessels in living tissue comprises two parts; one for measuring infrared absorption and one for laser doppler flowmetry.

Figure 5:
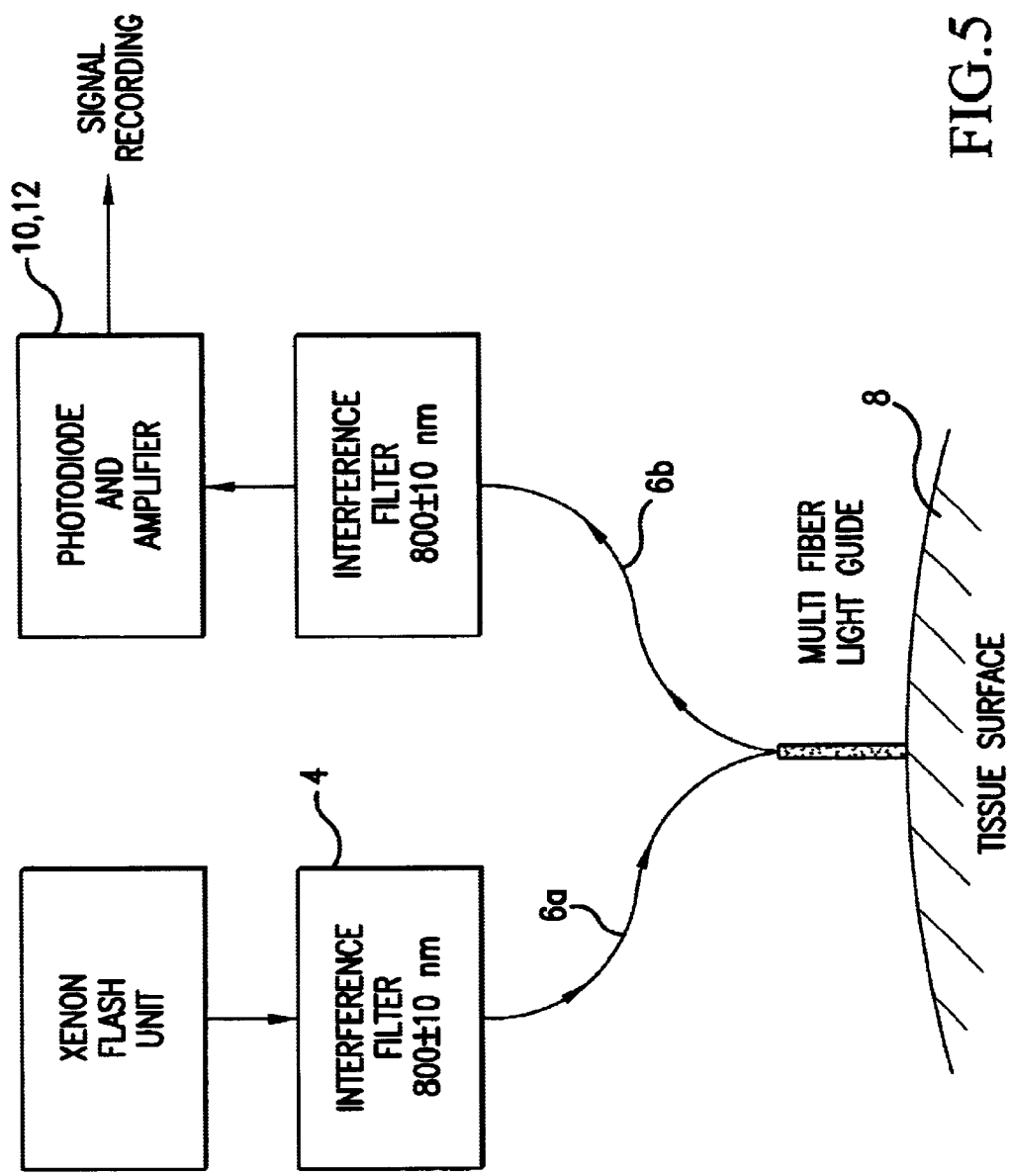
FIGS. 5 and 6 show a schematic outline of the apparatus for measuring near infrared absorption.
Figure 6:
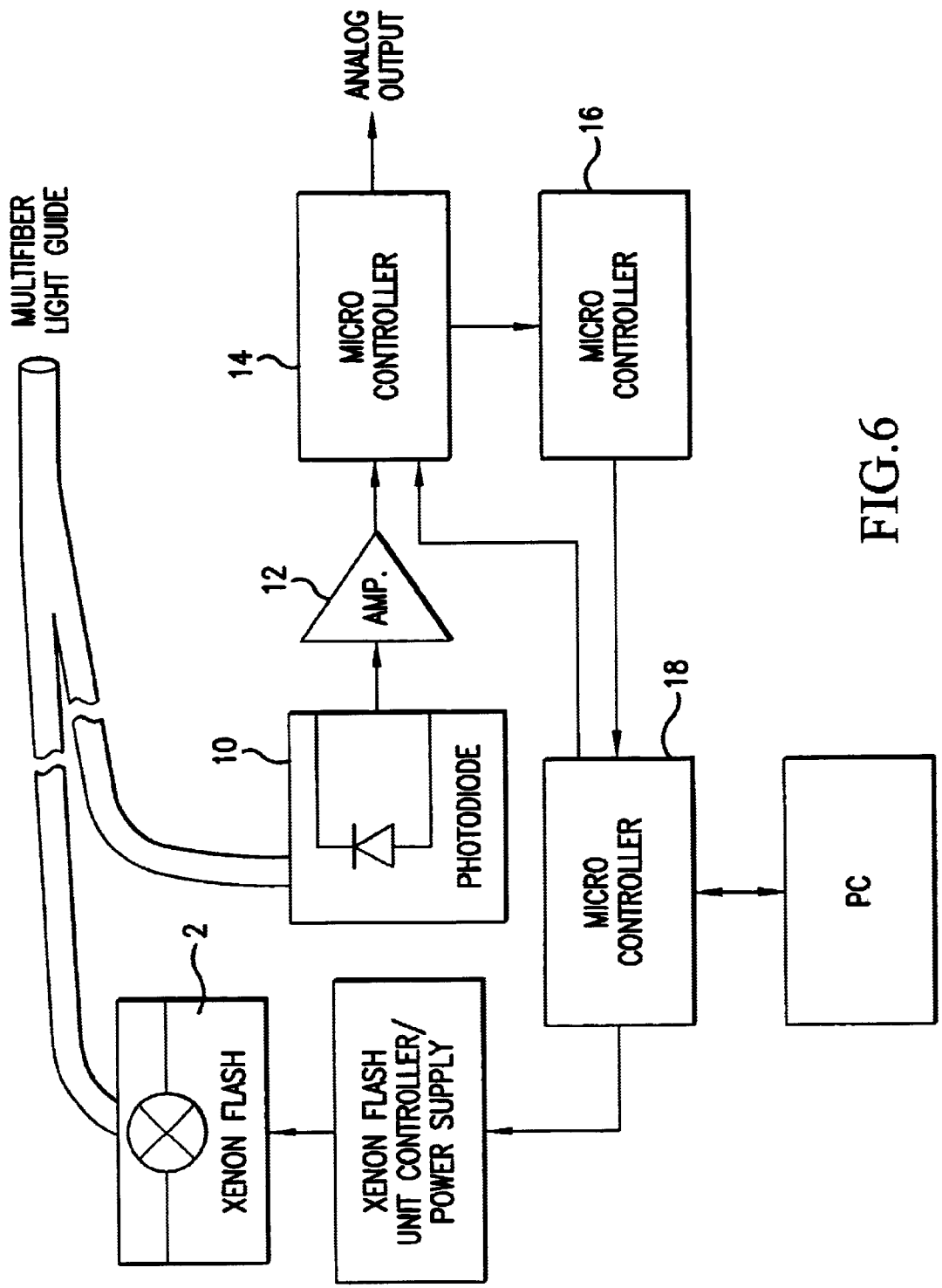
Figure 7A:
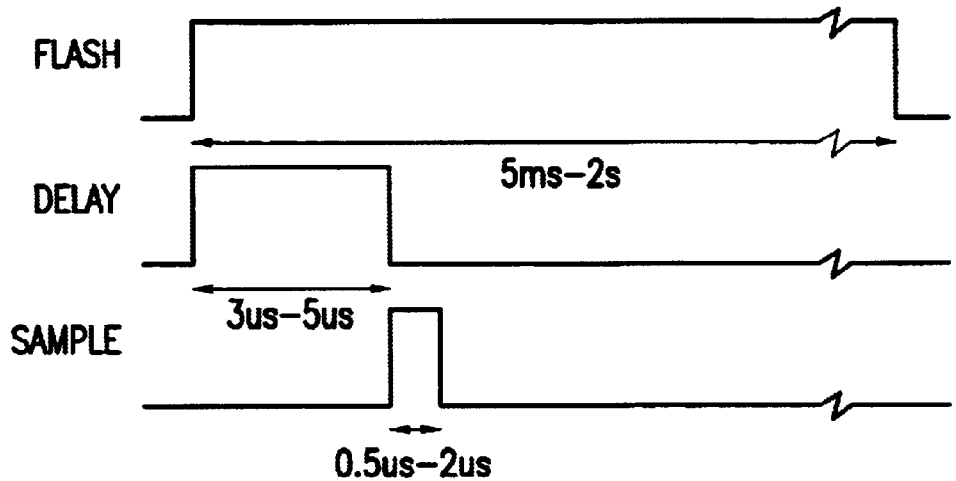
FIG. 7a illustrates the pulses for controlling the apparatus, illustrated in FIGS. 5 and 6.
Figure 7B:
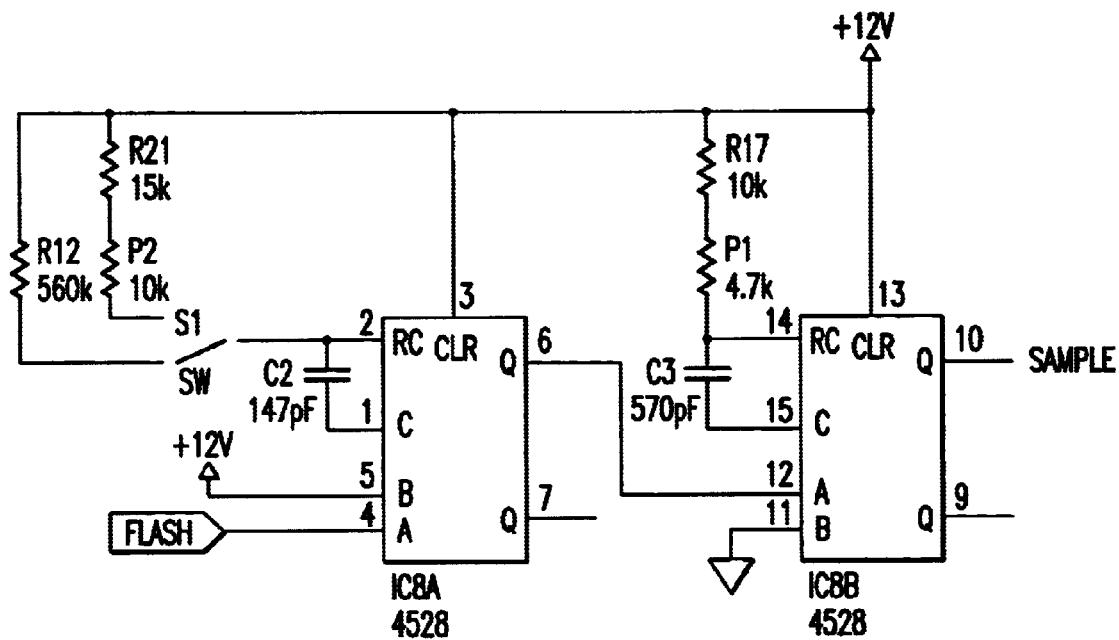
FIG. 7b shows the circuits for providing the pulses.
Figure 8:
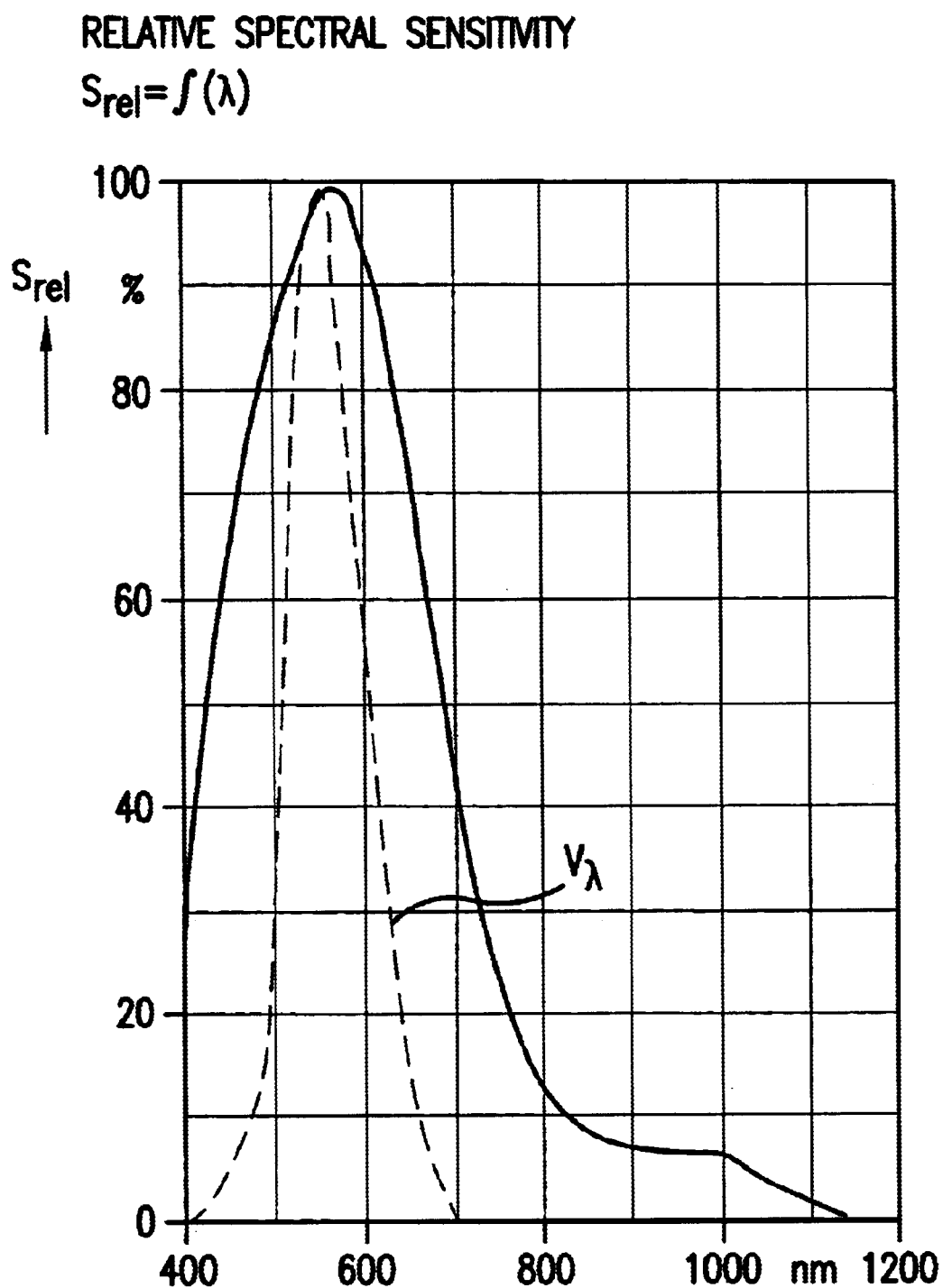
FIG. 8 shows the relative spectral sensitivity of the photo diode.

A schematic outline of the apparatus for measuring near infrared absorption at 800 nm (the isospestic point of the deoxy-hemoglobin/oxy-hemoglobin spectrum, i.e. a wave length at which there is no change in absorbtion due to tissue oxygenation changes) is shown in the block diagram on FIGS. 5 and 6. The apparatus comprises a light source 2, in form of a xenon flash unit (Xenon flash L4633 Hammatsu Co, Inc.) which via an optical filter (an interference filter 4) results in an emission of light having a wavelength of 800±10 nm through one branch 6a of an Y-shaped optical fiber coupled to the tissue 8. The flash has a rise time of 0.6 $\mu$sec and a peak width of approximately 2 $\mu$sec. The light reflected from the tissue 8, i.e. the light which has not been absorbed, is transmitted through the other branch 6b of the Y-shaped optical fiber and a second optical filter (an interference filter, 800±10 nm) to a photo diode 10 (Siemens BPW21 photo diode). An electrical signal corresponding to the light received by the photo diode is transmitted to an amplifier 12 and from there to a sample and hold circuit 14—see FIG. 6. The sample and hold circuit 14 has a variable amplification so as to obtain an output signal in the range from 0–5 volt at an in-port of an A/D converter 16. Alternatively the signal may be taken out to an analog strip chart recorder. A micro controller 18 controls a trigger signal for the xenon flash unit 2 and the sample and hold circuit 14 respectively (see configuration in FIG. 7a). Data collection is performed by means of a PC which is connected to a micro controller 18. The software in the micro controller 18 allows for setting of the variable amplification of the sample and hold circuit 14 as well as the repetition frequency for the measurement. FIG. 7b illustrates the circuit for providing the sample pulse by means of the flash pulse. The sample pulse is delayed in relation to the flash pulse (conf. FIG. 7a). The requirement for the sample and hold circuit is that the signal level must be maintained for at least 10 msec corresponding to the maximum 100 Hz repetition frequency of the xenon flash unit. This implies that the time constant of the sample and hold circuit is 10 msec.

The above mentioned apparatus has proved to give reproducible measurements of light absorption at 800 nm, due to the use of a Y-shaped optical fibre which secures optimal optical coupling between the tissue surface and the instrument.

The apparatus could be used for non-invasive quantification of angiogenesis or quantification of destruction of existing blood vessels in living tissue and comprises a xenon flash unit, an optical filter, and a Y-shaped optical fiber-bundle where one branch of the fiber-bundle is coupled to the flash unit and the other branch of the fiber bundle is coupled to a detection unit, while the merged part of the fiber bundle is adapted to couple the apparatus to the tissue.

Figure 9:
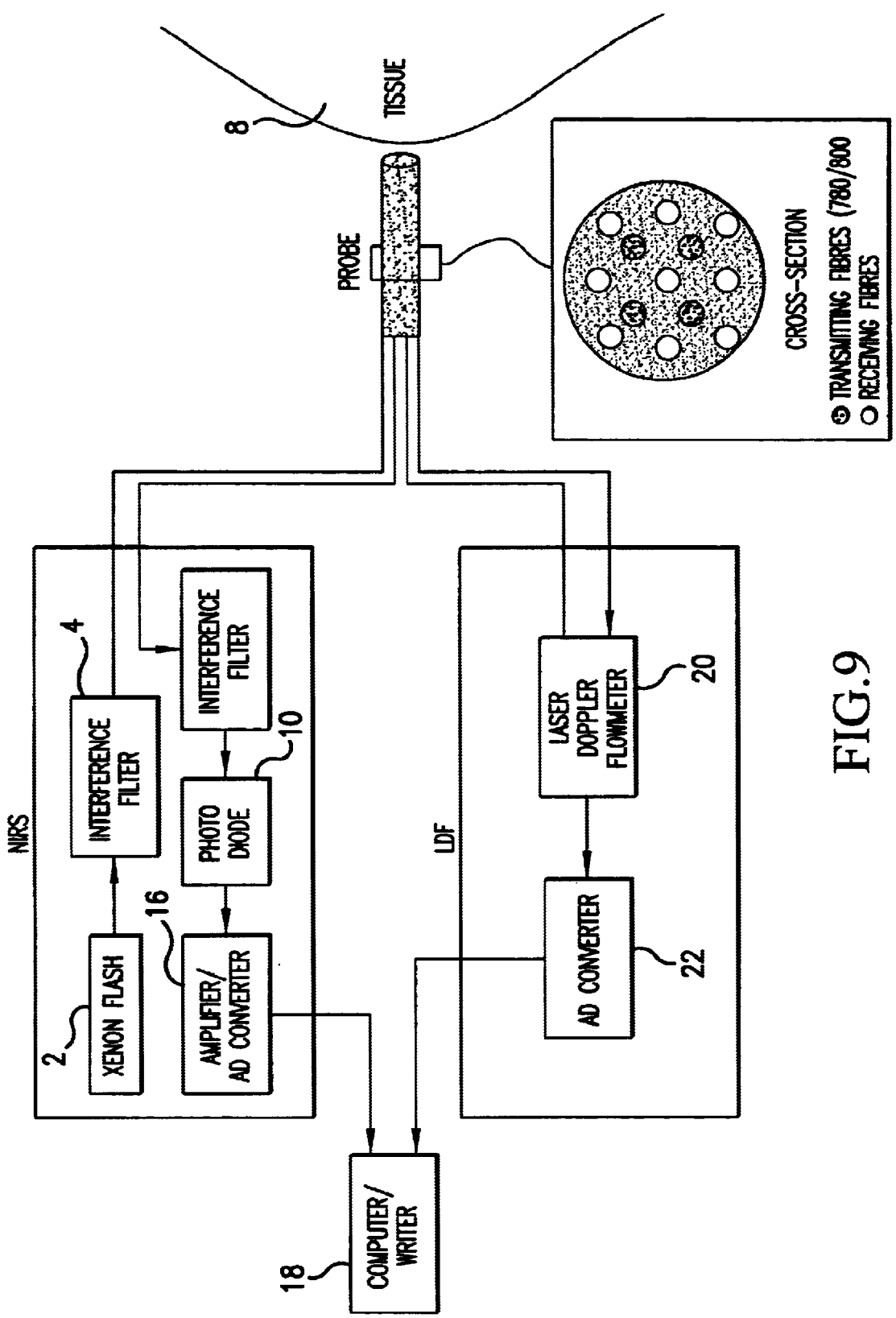
FIG. 9 shows the combined apparatus for measuring both near infrared spectroscopy and laser doppler flowmetry at the same spot.

In a preferred embodiment according to the invention the above mentioned apparatus is combined with a Laser Doppler Flowmeter (LDF) for measuring perfusion rate. This combined system is shown in FIG. 9 and comprises an apparatus for measuring infrared absorption (NIRS) and an apparatus for measuring perfusion rate (LDF), via the fused LDF and the NIRS lightconductors (see FIG. 10). The apparatus for measuring perfusion rate comprises a laser doppler flowmeter 20 which through an optical fiber emits a laser light pulse of a different wavelength compared to the one used in the absorption measurement. The light pulse reflected by the tissue 8 is transmitted via a second optical fiber in close proximity to the first, which is used for the absorption measurement. The reflected laser light pulse is returned to the flowmeter 20 correlating the frequency of the reflected light pulse to the frequency of the original emitted light pulse. From the frequency displacement and the light pulse it is possible to estimate the local perfusion rate in the tissue. A signal representative of the frequency shift is transmitted to an A/D converter 22 from where the digitized signal is transmitted to a micro controller 18 also controlling the apparatus for measuring infrared absorption.

The optical fibers of the apparatus for measuring perfusion rate and the optical fibers of the apparatus for measuring infrared absorption are preferably built into one and the same optical fibre bundle in such a way that both types of measurements are performed at the same locus. This can be obtained by packing the NIRS optical fibers outside of the LDF optical fibers (see the cross-section of the probe in FIG. 10).

Figure 10:
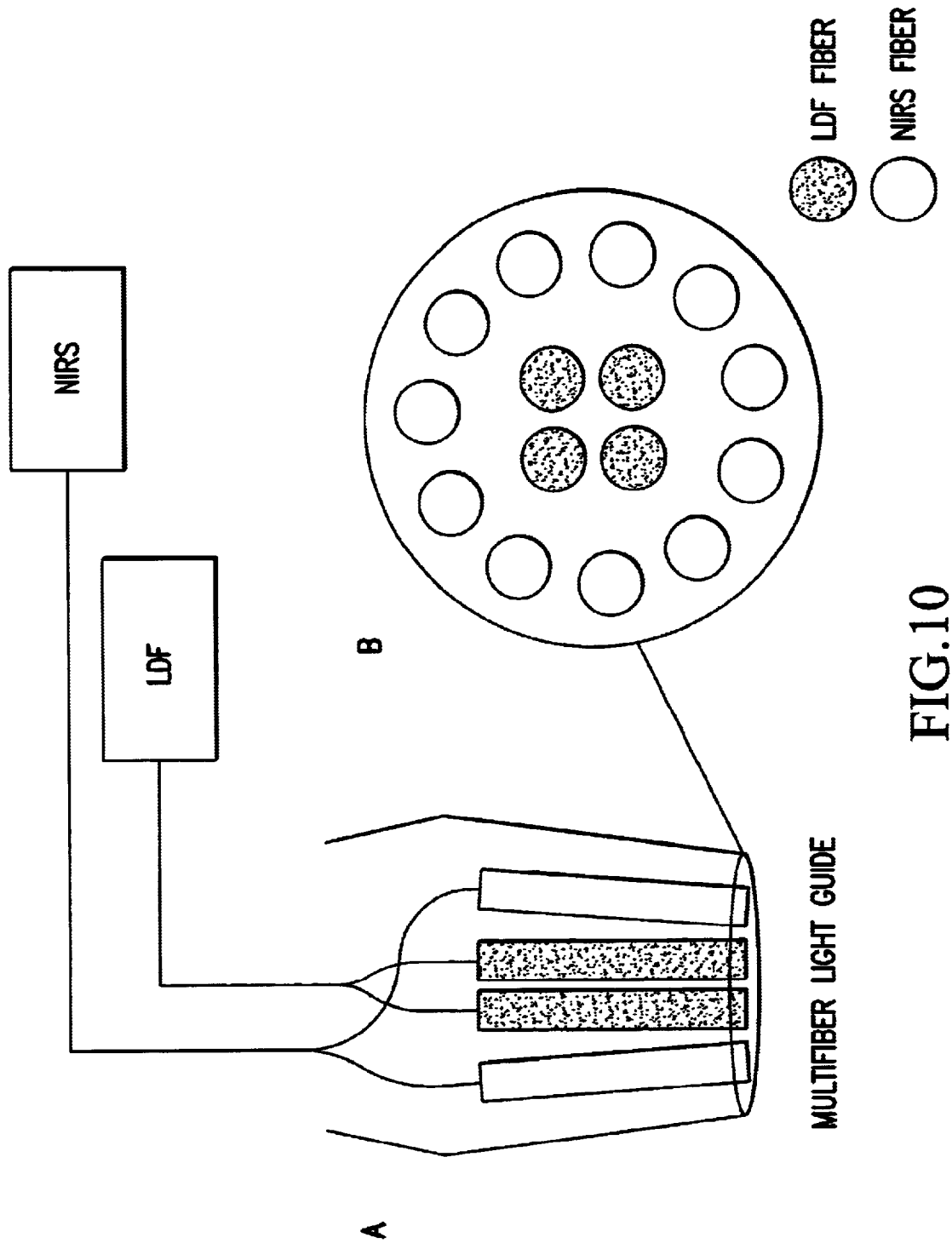
FIG. 10 shows the integration of the LDF fibers and the NIRS fibers in to a combined probe.

Both the LDF and the NIRS method provides global measurements. Since the wavelengths applied by the two measurements are close to each other (780 nm and 800 nm, respectively), the NIRS and LDF signals will originate from nearly the same tissue volume, provided the optical geometry of the two methods are comparable. In order to meet this requirement, we have constructed a NIRS/LDF probe by physically combining the two probes as shown in FIG. 10. This probe design does not result in significant cross-talk between the two systems. I.e. in a given fixed position on a tissue one signal is not significantly affected by turning on or turning off the other instrument.

Furthermore, the measurements can be performed either (i) displaced in time, i.e. one second the NIRS signals are recorded and the next second the LDF signals, or (ii) simultaneously, in which case the signals have to be separated by means of appropriate interference filters.

In the following some illustrating examples will be given.

EXAMPLE 1

The apparatus as shown on FIG. 9 was tested in a mouse model with a controlled angiogenic response induced by local application of an angiogenic agent, basic fibroblast growth factor (bFGF). Parallel experiments were performed with identical setup in order to correlate the sensitivity of near infrared spectroscopy (NIRS) compared to laser doppler flowmetry (LDF) for estimation of angiogenic and anti-angiogenic responses.

Figure 1B:
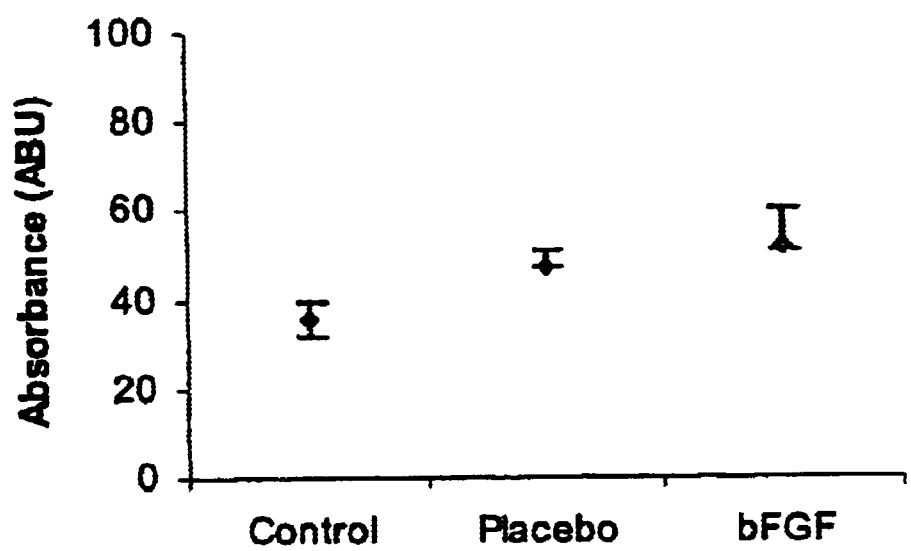
FIG. 1B shows the induced angiogenic response in a mouse model after application of fibroblast growth factor (bFGF) measured by NIRS.

A slow release pellet (Innovative Res.) containing 100 micrograms of bFGF released at a constant rate over 10 days was implanted under the skin at three different locations in the mouse. The angiogenic response to the active substance was evaluated in comparison with placebo pellets. FIG. 1A shows LDF recordings on controls (n=16), i.e. on placebo pellets immediately after implantation, and on placebo (n=23) and bFGF (n=23) on day 6 after implantation. LDF recordings on bFGF were significantly higher than placebo (p<0.05) and controls (p<0.001), and placebo was significantly higher than controls (p<0.001). FIG. 1B shows NIRS recordings on controls (n=16), i.e. on placebo pellets immediately after implantation, and on placebo (n=15) and bFGF (n=15) on day 7 after implantation. NIRS recordings on bFGF were significantly higher than placebo (p<0.05) and controls (p<0.001), and placebo was significantly higher than controls (p<0.001). Median values and interquartile range is shown.

A statistically significant increase in absorption and perfusion was seen (FIG. 1 A/B) in the induced animals, demonstrating that the technique can detect induced angiogenesis.

EXAMPLE 2

Figure 2:
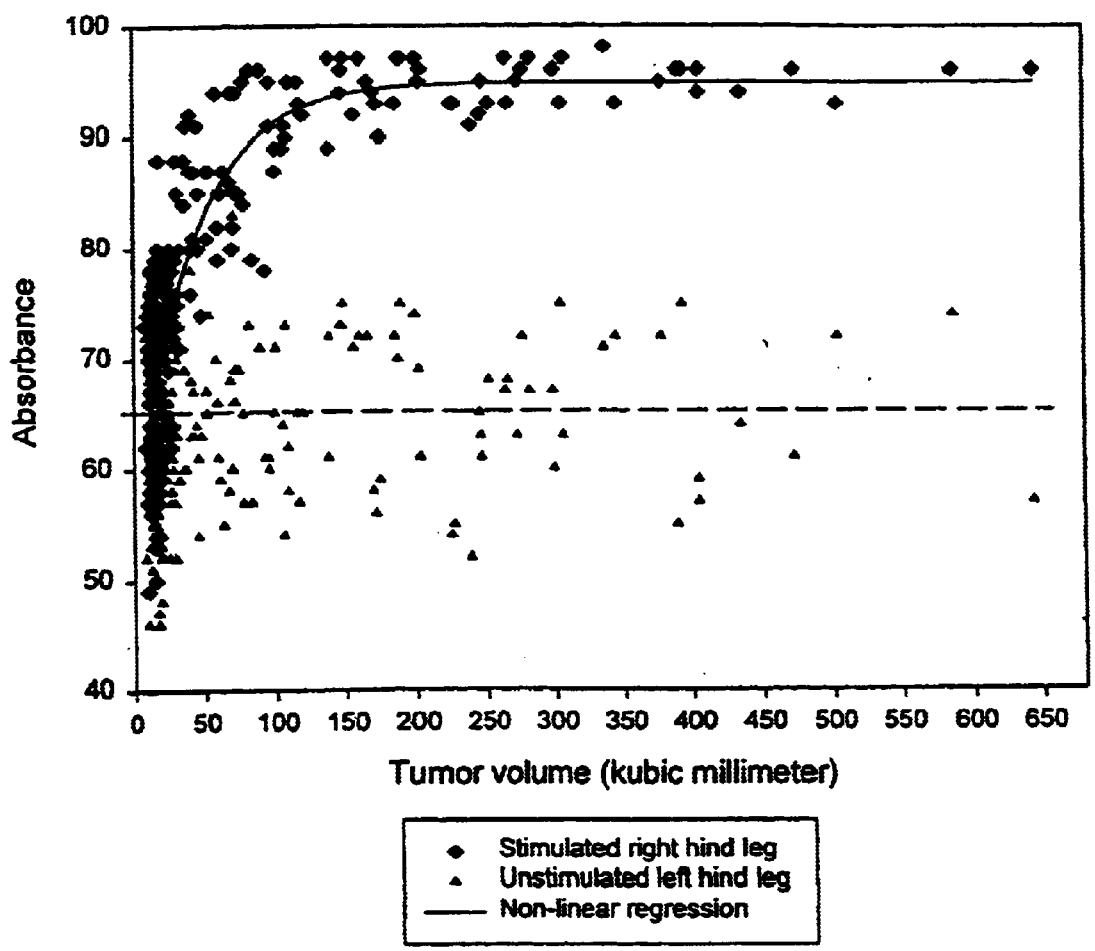
FIG. 2 shows the angiogenic response induced by local application of xenotransplanted human cancer tissue in a mouse model.

The apparatus as shown on FIG. 9 was tested in a mouse model with a controlled angiogenic response induced by local application of xenotransplanted human cancer tissue as the source of angiogenic stimulus. Implants with human tissue with very high expression of angiogenic factors (U-87, a human glioblastoma multiform) was repeatedly examined during growth. When the tumor transplants reached a certain size, the absorption reached a maximum (FIG. 2), which appeared to be specific for individual tumor types, and correlated closely to the angiogenic activity as evaluated by expression (protein and mRNA levels) of angiogenic factors and by histological estimates of vessel density. Other tumor lines (U118, U373, 54A, 54B and DMS79), some with a much lower angiogenic activity than U-87, were also tested in a similar experiment. They all reached a specific maximum characteristic of each tumor.

EXAMPLE 3

The ability to detect anti-angiogenic properties of therapeutic agents in these preparations was tested in the same technical settings by comparing treated versus untreated animals. Significant anti-angiogenic activity was demonstrated during treatment with a specific anti-angiogenic compound, TNP-470 (FIGS. 3A and 3B) which is a selective inhibitor of endothelial cell proliferation, and with dexamethasone (FIGS. 3C and 3D) which is a synthetic glucocorticoid analogue.

Figure 3A:
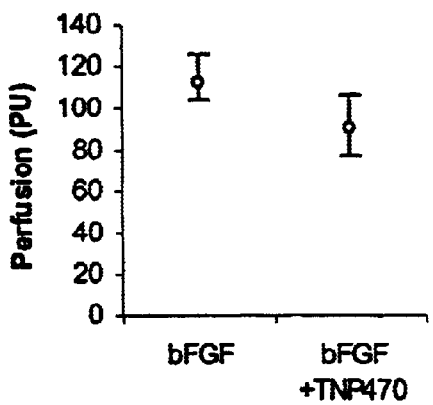
FIGS. 3A and 3B show the anti-angiogenic effect of treatment with a specific anti-angiogenic compound, TNP-470.
Figure 3B:
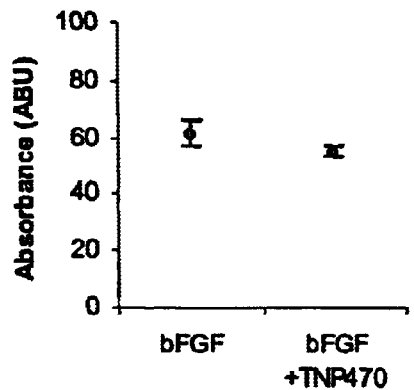
Figure 3C:
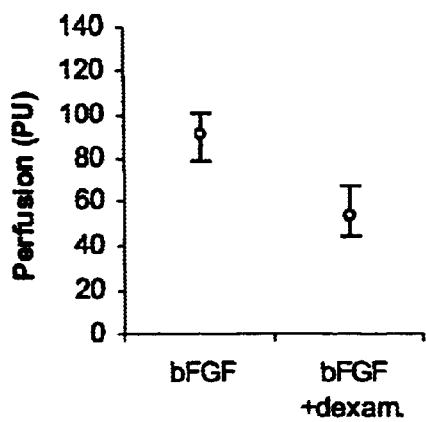
FIGS. 3C and 3D show the anti-angiogenic effect of dexamethasone.
Figure 3D:
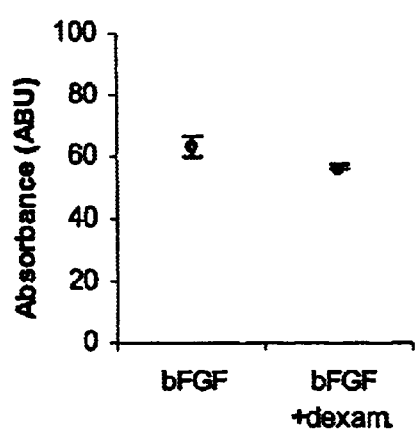

FIGS. 3A and 3B show the anti-angiogenic activity after treatment with TNP-470 (7 mg/kg q.d.x7, n=13). LDF (p<0.05) and NIRS (p<0.05) recordings were significantly lower compared to untreated bFGF stimulated animals (n=14). FIGS. 3C and 3D show the anti-angiogenic activity after treatment with dexamethasone (10 mg/kg q.d.x7, n=12), LDF (p<0.001) and NIRS (p<0.001) recordings were significantly lower compared to untreated bFGF stimulated animals (n=14). LDF recordings were performed on day 6, whereas NIRS recordings were performed on day 7 after implantation. Median values and interquartile range is shown.

EXAMPLE 4

Figure 4:
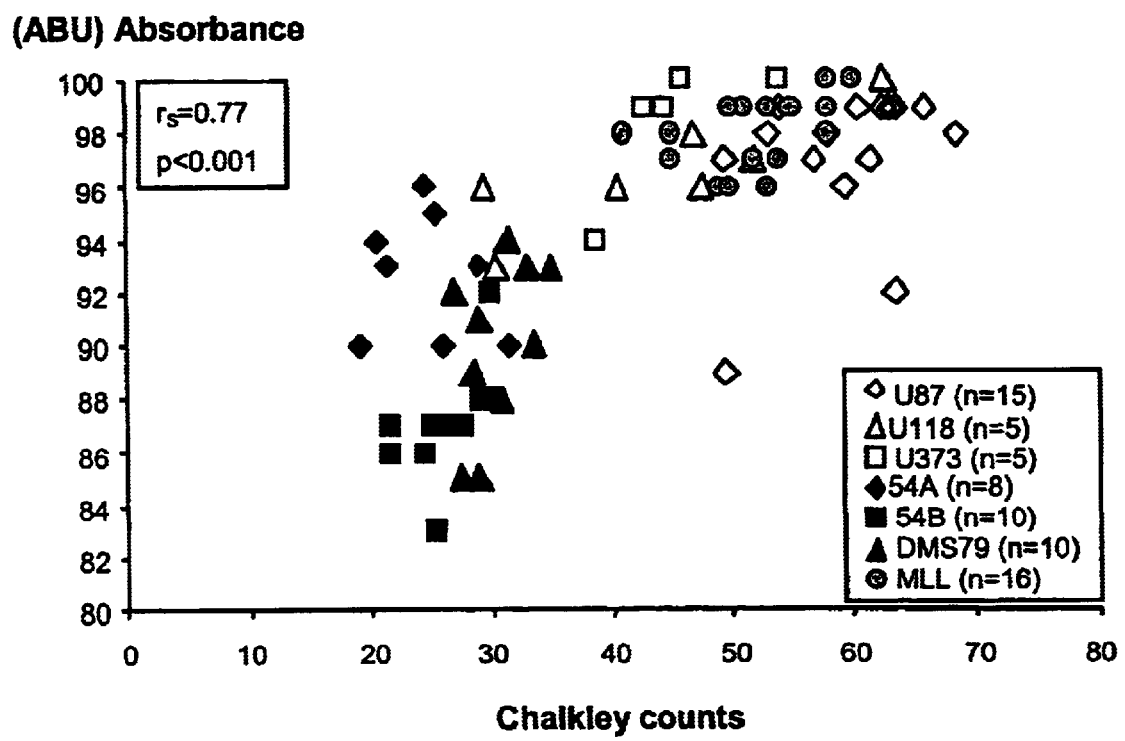
FIG. 4 shows the correlation between non-invasive measures of tumor hemoglobin concentration by NIRS and estimates of vessel density by Chalkley counts.

The relationship between non-invasive measures of tumor hemoglobin concentration by NIRS and estimates of vessel density by Chalkley counts was examined in seven tumor lines (gliomas: U87, U118, U373; Small Cell Lung Cancer (SCLC): 54A, 54B, DMS79; rat prostate cancer: MLL) on the hind leg of nude mice. Chalkley counts were obtained from CD31 immunostained cryosections. The NIRS absorbance increased with the tumor size until a tumor line specific plateau was reached from tumor sizes of 100–150 mm$^3$. FIG. 4 shows that NIRS absorbance and vessel density of the tumors were strongly correlated ($r_s$=0.77, p<0.001, n=69), thus indicating that NIRS provides a non-invasive estimate of the tumor vessel density that can be used as a reliable estimate of tumor vascularization.

We also evaluated the correlation between tumor size and NIRS recordings during untreated growth for all seven tumor lines, and during continuous anti-angiogenic treatment with TNP-470 for two tumor lines, U87 and MLL. Continuous treatment with TNP-470 significantly retarded the onset of tumor growth and the growth rate. When comparing treated and untreated tumors of similar size, the final NIRS recordings and Chalkley counts were significantly lower in TNP-470 treated tumors. In conclusion, the NIRS technique can provide reliable non-invasive measures of the tumor vasculature and its modification during untreated growth as well as during anti-angiogenic therapy.

EXAMPLE 5

Anti-vascular effects on C3H murine mammary carcinoma were determined by combined LDF and NIRS measurements, in mice with tumor transplants using the apparatus shown in FIG. 9.

The three agents DMX-AA, FAA and CA4B are antivascular agents, which by various mechanisms cause collapse of tumor vasculature and consequently a decrease in tumor blood flow and oxygenation. Hydralazine (HDZ) is a well known anti-hypertensive agent that causes peripheral vasodilatation, i.e. a drop in vascular flow resistance leading to an acute decrease in tumor perfusion (a.k.a. the "steal effect"), because of the lack of autoregulation of tumor vessels. The anti-vascular effect of the four drugs is shown in table 1. Numbers in the table represent differences between post- and pre-treatment measurements expressed as percent of the pre-treatment value. Number of experiments per drug=3.

TABLE 1

Determination of anti-vascular effects on the C3H murine mammary carcinoma by combined LDF and NIRS measurements, in mice with tumor transplants.
N = 3 per drug, median values (range)

| Drug | LDF | NIRS* | pO$_2$ after treatment median | % < 5 mm Hg |
|---|---|---|---|---|
| FAA | −34% | +6% | 1.5 | 69% |
| 150 mg/kg i.p. | (11–74) | (3–25) | (0.4–2.5) | (60–86) |
| CA4B | −65% | +2% | 1.5 | 91% |
| 250 mg/kg i.p. | (28–70) | (−8–50) | (0.9–1.9) | (85–100) |
| DMX-AA | −74% | +1% | 2.8 | 66% |
| 20 mg/kg i.p. | (—) | (−2–3) | (0.8–3.9) | (60–95) |
| HDZ | −93% | +36% | 1.9 | 85% |
| 5 mg/kg i.p. | (92–96) | (22–50) | (0.7–3.6) | (79–100) |
| Controls | | | 5.3 ± 0.8 | 53 ± 7% |

*NIRS recordings are expressed in arbitrary units of reflectance (1/absorbance), i.e. an increased NIRS value corresponds to a decrease in hemoglobin concentration.

All four agents caused a decrease in tumor blood perfusion estimated by LDF and in tumor oxygenation. By the combined measurements of LDF and NIRS it was possible to show a distinction between the mode of action of the three antivascular agents (FAA, CA4B, DMX-AA), which traps the tumor blood pool resulting in a decrease in perfusion and an unchanged hemoglobin concentration, and Hydralazine (HDZ) which drains the tumor blood pool resulting in a decrease in perfusion and a decrease in hemoglobin concentration. This illustrates the advantages of the combination of LDF and NIRS for the determination of effects and mechanism of action of experimental agents targeting the tumor vasculature.

We claim:

1. An apparatus for non-invasive local determination of blood vessel formation in living tissue comprising
    a xenon flash unit,
    an optical filter,
    a Y-shaped optical fiber-bundle, one branch of the fiber-bundle being coupled to the flash unit and the other branch of the fiber-bundle being coupled to the detection unit, and the merged part of the fiber-bundle being adapted to couple the apparatus to the tissue to be tested, and
    a laser Doppler flowmeter.

2. The apparatus according to claim 1, wherein the light absorption detection unit comprises a photo-diode and amplifier, a sample and hold circuit and A/D converter, and a micro controller for controlling the frequency of the measurements, said micro controller being connected to a PC for evaluating and displaying the measurement results.

3. The apparatus according to claim 1, wherein an optical filter is placed in front of the detection unit, said filter being an interference type filter (800 nm +/−10 nm), with a collecting lens forming the light guide image on the photo-diode.

4. A non-invasive method for local determination of blood vessel formation of a subject, which comprises
    (i) measuring the total hemoglobin concentration of the subject using near infrared spectroscopy, and substantially at the same time;
    (ii) measuring average blood perfusion using laser Doppler flowmetry,
wherein the two measurements (i) and (ii) are performed at substantially the same position on the subject.

5. The method according to claim 4, wherein the near infrared spectroscopy measurement and the laser Doppler flowmetry measurement are performed with the same probe.

6. The method according to claim 5, wherein the agent that affects blood circulation comprises at least one an anti-angiogenic agent, vascular targeting agent, and/or anti-inflammatory agent.

7. The method according to claim 4, wherein the steps (i) and (ii) are performed after administration to the subject of an agent that affects blood circulation.

8. The method according to claim 4, wherein the steps (i) and (ii) are performed on a skin transplant.

9. The method according to claim 4, wherein the steps (i) and (ii) are performed repeatedly during an extended time period.

* * * * *